United States Patent [19]

Pews

[11] Patent Number: 4,851,594
[45] Date of Patent: Jul. 25, 1989

[54] SUBSTITUTED OXIRANE COMPOUNDS

[75] Inventor: R. Garth Pews, Midland, Mich.

[73] Assignee: The Dow Chemical Company, Midland, Mich.

[21] Appl. No.: 887,758

[22] Filed: Jul. 21, 1986

Related U.S. Application Data

[62] Division of Ser. No. 665,221, Oct. 26, 1984, Pat. No. 4,629,492.

[51] Int. Cl.$^4$ .............................................. C07C 25/13
[52] U.S. Cl. .................................. 570/128; 549/563; 549/525; 71/126; 71/88; 570/127
[58] Field of Search ............... 570/128, 127, 182, 185; 549/525, 563, 579

[56] References Cited

U.S. PATENT DOCUMENTS

| | | | |
|---|---|---|---|
| 3,336,401 | 8/1967 | Morris | 71/125 |
| 3,391,203 | 7/1968 | Decker | 570/185 |
| 3,719,465 | 3/1973 | Ozretich | 71/88 |
| 3,888,888 | 6/1975 | Pallos et al. | 549/563 |
| 3,930,835 | 1/1976 | Ozretich | 71/88 |
| 3,998,856 | 12/1976 | Rosenberger | 549/579 |
| 4,013,772 | 3/1977 | Ozretich | 71/88 |
| 4,018,801 | 4/1977 | Ozretich | 549/563 |
| 4,211,549 | 7/1980 | Markley et al. | 71/88 |
| 4,629,492 | 12/1986 | Pews | 71/88 |
| 4,632,999 | 12/1986 | Zerbes et al. | 549/579 |

OTHER PUBLICATIONS

H. Kimoto et al., Bull. Chem. Soc. Japan, vol. 49(6) (1976), pp. 1642-1649.

Primary Examiner—Richard L. Raymond
Assistant Examiner—A. A. Owens
Attorney, Agent, or Firm—S. Preston Jones; Ronald G. Brookens

[57] ABSTRACT

Novel substituted styrene compounds of the formula

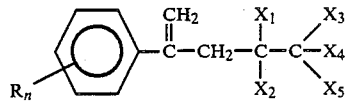

wherein R is halogen or —CF$_3$; n is an integer from 0 to 5; and X$_1$, X$_2$, X$_3$, X$_4$ and X$_5$ are halogen, and are useful as intermediates for preparing herbicidal compounds.

8 Claims, No Drawings

SUBSTITUTED OXIRANE COMPOUNDS

This application is a divisional of application Ser. No. 665,221 filed Oct. 26, 1984 now U.S. Pat. No. 4,629,492.

BACKGROUND OF THE INVENTION

The invention relates to novel herbicidal epoxy pentanes useful in the control of undesirable plants, or weeds.

Attention is called to the following references for the disclosure of oxirane compounds: U.S. Pat. Nos. 3,719,465 to Ozretich; 3,930,835 to Ozretich; 4,013,772 to Ozretich; 4,018,801 to Ozretich; 4,211,549 to Markley et al; and to the Bull. Chem. Soc. Jpn. (1976), 49(6), 1642-9. All these reference are incorporated herein by references.

SUMMARY OF THE INVENTION

This invention relates to herbicidal compositions and methods utilizing novel substituted oxirane compounds as active ingredients. According to the present invention, there are provided herbicidal compositions containing compounds of the Formula (I):

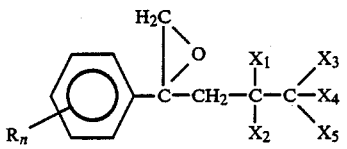

wherein each $R_n$ independently represents halogen, or $CF_3$; n is an integer from 0 to 5; and $X_1$, $X_2$, $X_3$, $X_4$, and $X_5$ independently represent halogen. The present invention has the advantage of providing a method for controlling both broadleaf and grassy weeds. Another advantage of the present invention is the control of weeds by either postemergence or preemergence application of the oxirane compounds to the locus of the weeds or weed seeds. Another advantage of the present invention is the control it provides of broadleaf and grassy weeds in economically important crops such as soybeans, cotton, white winter wheat, corn, grain sorghum, sugar beets, rape, and cultivated rice. And still yet another advantage of the present invention is the excellent control it provides of undesirable weeds such as nutsedge, pigweed, crabgrass, Johnsongrass, barnyard grass, wild oats, yellow foxtrail, velvet leaf, Jimson weed, and morning glory.

DETAILED DESCRIPTION OF THE INVENTION

The term "herbicide" is used herein to mean a chemical compound or composition thereof used to control, suppress, or kill plants, or to severely interrupt their normal growth processes, as defined in the Herbicide Handbook of the Weed Science Society of America, 5th Edition, (1983), 309 West Clark Street, Champaign, Ill., incorporated herein by reference. By "growth controlling" or "herbicidally-effective amount" is meant an amount of active ingredient which causes a modifying effect on plants and includes deviations from natural development, killing, regulation, dessication, retardation, and the like. The term "plants" is meant to include germinating seeds, emerging seedlings and established vegetation. The term "active ingredient" is defined as the chemical in a herbicide formulation primarily responsible for its phytotoxicity. By "preemergence operation" is meant the application of the herbicidal compound to the soil prior to emergence of the specified weed or crop. By "postemergence operation" is meant the application of the herbicidal compound after the emergence of the specified weed or crop.

As used herein, the term "phenyl ring" refers to the univalent $C_6H_5$ group derived from benzene and characteristic of phenol and other benzene derivatives; as defined in "The Condensed Chemical Dictionary", 10th Edition, Reinhold Publishing Co. N.Y. (1981), incorporated herein by reference. The term "halogen" represents bromine, chlorine, fluorine, and iodine.

The active ingredients of the present invention are generally oils or crystalline solids at ambient temperatures which are soluble in many organic solvents commonly employed as herbicidal carriers. The active ingredients of the above Formula (I) wherein each R is chlorine constitute a preferred embodiment of the present invention. Active ingredients wherein each R group is the same constitute a further preferred embodiment. An additional preferred class of compounds are those in which R is —$CF_3$. Preferably, n is an integer from 1 to 3; most preferably n is 1 to 2. Also preferred are embodiments where R is substituted at the 3 or at the 3 and 5 positions on the phenyl ring. An especially preferred class are those compounds where R, $X_1$ and $X_2$ are chloro and $X_3$, $X_4$ and $X_5$ are fluoro. Especially preferred compounds include 2-(3-chlorophenyl)-2-(2,2-dichloro-3,3,3-trifluoropropyl)oxirane; 2-(3,5-dichlorophenyl)-2-(2,3-dichloro-2,3,3-trifluoropropyl)oxirane; 2-(2,2-dichloro-3,3,3-trifluoropropyl)-2-(3-(trifluoromethyl)phenyl)oxirane; most preferably 2-(3,5-dichlorophenyl)-2-(2,2-dichloro-3,3,3-trifluoropropyl)oxirane.

The active ingredients of the above Formula (I) are readily prepared by the reaction of a substituted styrene compound of the Formula (II)

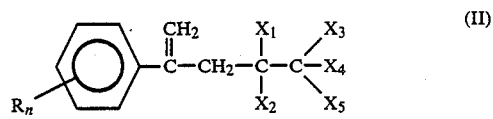

wherein $R_n$, $X_1$, $X_2$, $X_3$, $X_4$ and $X_5$ are as defined hereinbefore, with a suitable percarboxylic acid reactant, as described in U.S. Pat. No. 3,930,835 incorporated herein by reference.

Representative and suitable percarboxylic acids which can be employed in the preparation of the active ingredients include, for example, perchloracetic acid, pertrifluoroacetic acid, perbenzoic acid, peracetic acid and the like. In preparing the present compounds of the present invention, either aqueous or nonaqueous buffer solutions of the acid reactants can be employed and are prepared by the use of an alkaline buffering agent, such as, for example, sodium acetate, sodium benzoate, carbonates, bicarbonates and the like.

In carrying out the reaction, the substituted styrene compound of Formula (II) is usually mixed with a reaction medium, such as for example, methylene chloride, chloroform, 1,2-dichlorobenzene and the like, and mixed slowly with the percarboxylic acid reactant in a buffer solution. While the amounts of the reactants to be employed are not critical, the reaction generally consumes reactants in the proportion of 1 mole of substituted styrene reactant to 1 or more moles of percarboxylic acid reactant. A suitable ratio of reactants is from about 1:1 to about 1:6 (substituted styrene:percarboxylic acid) and the employment of the reactants in a mole ratio of from about 1:3 moles is preferred. The reaction is usually conducted at temperatures between about 20° and 120° C. preferably 40° C., and is ordinarily carried out under ambient atmospheric pressure.

The resulting reaction mixture is usually maintained, with stirring, for a period of time sufficient to provide for substantial completion of the reaction. Generally the reaction mixture is stirred at ambient temperatures for a period of from about 24 to about 100 hours or more. Recovery of the desired product from the reaction mixture is achieved by employing conventional procedures. Typically, the reaction mass is washed with water and neutralized with a sufficient amount of a base, e.g., sodium carbonate or the like, before being concentrated to dryness under reduced pressure.

The substituted styrene compounds employed as starting materials can be prepared in accordance with known or analogous methods. See, for example, U.S. Pat. Nos. 3,391,203 and 3,336,401 incorporated herein by reference.

Generally, the substituted styrene compounds may be prepared by reacting an α-methylstyrene with a polyhalogen compound of the formula

wherein X and Y are independently halogen as defined hereinbefore, with the proviso that X and Y are not both fluorine; and W and Z independently represent halogen, —CF$_3$, —CX$_2$F, —CXF$_2$, lower alkyl, cyano, carboxylic acid derivatives, aldehydes, or ketones. The α-methylstyrene is reacted with the polyhalogen in the presence of a transition metal salt, such as CuCl, with or without co-catalysts such as amines and phosphines. Polyhalogens, α-methylstyrenes, and transition metal salts are compounds well known to one skilled in the art.

The following examples are presented to illustrate preparation of typical compounds employed in the invention, but the scope of the invention is not to be considered limited to the specific examples given.

EXAMPLE 1

Preparation of 2-(3,5-dichlorophenyl)-2-(2,2-dichloro-3,3,3-trifluoropropyl)oxirane:

The compound was prepared from 3,5-dichloro-α-methylstyrene and 1,1,1-trichlorotrifluoroethane as follows: 3,5-dichloro-α-methylstyrene (10 g), 1,1,1-trichlorotrifluoroethane (20 g), cuprous chloride (3.0 g) and cyclohexylamine (3.0 g) were heated and mixed with a magnetic stirrer in a glass ampoule overnight at 110° C. Extraction of the mixture with methylene chloride and water gave the intermediate 1,3-dichloro-5-(3,3,-dichloro4,4,4-trifluoro-1-methyl-1-chlorobutyl)-benzene. The mass and NMR spectra for this first intermediate were consistent. This first intermediate was diluted with 50 ml of 1,2-dichloroethane, 0.5 g of anhydrous FeCl$_3$ was added, and the mixture refluxed for 2 hours. Extraction of the mixture with dilute washes of aqueous HCl to remove the FeCl$_3$, followed by subsequent drying and distillation, gave a second intermediate. The NMR and mass spectra for this second intermediate was consistent for the compound 1,3-dichloro-5-(3,3-dichloro-4,4,4-trifluoro-1-methylene butyl)benzene (6 g), boiling point (bp) of 70° C. at (0.5 mm Hg). Calculated for C$_{11}$H$_7$Cl$_4$F$_3$: C, 39.08; H, 2.07; Cl, 41.98; F, 16.87. Found: C, 39.10; H, 2.10 Cl, 40.9; F, 16.0. Then a 4.0 g portion of this second intermediate was refluxed in 25 ml of 1,2-dichloroethane along with 4 g of 85% metachloroperbenzoic acid (MCPBA) for 2 hours to give the crude epoxide. The crude epoxide was isolated by extraction, dilution with benzene and filtration through silica gel. The benzene was removed under vacuum to give a colorless oil. NMR and mass spectra of the purified epoxide was consistent with the structure for 2-(3,5-dichlorophenyl)-2-(2,2-dichloro-3,3,3-trifluoropropyl)oxirane. Calculated for C$_{11}$H$_6$Cl$_4$F$_3$O: C,37.3; H, 2.09; Cl, 40.01: F, 14.85. Found: C, 37.46: H; 2.08; Cl 38.9; F, 15.3.

EXAMPLE 2

Preparation of 2-(3,5-dichlorophenyl)-2-(2,3-dichloro-2,3,3-trifluoropropyl)oxirane:

The above compound was prepared from 3,5-dichloro-αmethylstyrene and 1,1,2-trichlorotrifluoroethane as follows: 3,5-dichloro-αmethylstyrene (20g) 1,1,2-trichlorotrifluorethane (20g), acetonitrile (30 ml), cuprous chloride (1 g) and triphenylphosphine (1 g) were heated at 160° C. in a 200 ml Hastelloy C Parr bomb for 16 hours. The product was poured onto water and extracted with benzene. The benzene extract was dried, evaporated and distilled to give about 10 g of the olefin, 1,3-dichloro5-(3,4-dichloro-3,4,4-trifluoro-1-methylene butyl)benzene bp 65–67 (0.2 mm Hg). Calculated for C$_{11}$H$_7$Cl$_4$F$_3$: C, 39.09; H, 2.07; Cl, 41.96; F, 16.86: Found: C, 39.30: H, 2.18; Cl, 41.20: F, 18.2. Approximately 3.5 g of the above olefin was diluted with 50 ml of dichloromethane and reacted with 5 g of meta-chloroperbenzoic acid at room temperature for 40 hours. The product was isolated by extraction and purified by liquid phase chromatography on a silica gel column. The product was eluted with 50:50 benzene-hexane. Concentration of the product by evaporating off the benzene-hexane gave a clear liquid. The IR and NMR spectra were consistent with 2-(3,5-dichlorophenyl)-2-(2, 3-dichloro-2,3,3-trifluoro)oxirane. Calculated for C$_{11}$H$_7$ Cl$_4$F$_3$O. C, 37.3; H, 1.98; Cl, 40.04; F, 14.85. Found: C, 37.46; H, 2.08; Cl, 40.20; F, 16.10.

EXAMPLE 3

Preparation of 2-(3-chlorophenyl)-2-(2,2-dichloro-3,3,3-trifluoropropyl)oxirane:

M-chloro-α-methylstyrene (1.53g), 1,1,1-trichloro-2,2,2-trifluoroethane (2.81g), cuprous chloride (0.50g) and triethylamine (0.50g) were placed in a small sealed ampoule equipped with a magnetic stirrer, heated and stirred at 110° C. overnight with 20 ml acetonitrile. After evaporation of the acetonitrile the residue was chromatographed on a silica gel column. Elution with ethyl acetate-hexane afforded 1.84g of crude product. Distillation on a Kugelrohr system gave product bp 90° C. (1mm Hg) as a pale yellow oil. The IR and NMR spectra were consistent with 1-chloro-3-(3,3-dichloro-4,4,4-trifluoro-1-methylenebutyl) benzene. Epoxidation with m-chloroperbenzoic acid in dichloromethane at room temperature for 72 hours, purification by column chromatography on silica gel and elution with 25% ethyl acetate-hexane gave a colorless oil. The IR and NMR spectra were consistent with 2-(3-chlorophenyl)-2-(2,2-dichloro-3,3,3-trifluoropropyl)oxirane.

EXAMPLE 4

Preparation of 2-(2,2-dichloro-3,3,3-trifluoropropyl)-2-(3-trifluoromethyl) phenyl)oxirane:

M-trifluoromethyl-α-methylstyrene was converted to the olefin, 1-trifluoromethyl-3-(3,3-dichloro-4,4,4-trifluoro-1-methylene butyl)benzene, in a manner similar to that described above for the monochlorophenyl derivative in Example 3. Epoxidation of the above olefin with m-chloroperbenzoic acid in 1,2-dichloromethane at room temperature for 48 hours in the presence of powdered $Na_2CO_3$ gave the desired product which was isolated as a colorless oil after purification and removal of the eluant by chromatography. The IR and NMR spectra were consistent with the structure for 2-(2,2-dichloro-3,3,3-trifluoropropyl)2-(3-(trifluoromethyl)-phenyl)oxirane.

Compounds of this invention are useful as herbicides. The most distinctive utility of the compounds is based upon their ability to inhibit the growth of objectionable plant life. This growth inhibition, or herbicidal activity may be demonstrated by contacting a plant structure with the subject compounds, which may take place either preemergently or on established plants. Preemergence application may be accomplished in either of two ways; by application of the compounds to the surface of the soil or by incorporation of the compounds into the surface layer of soil.

In particular, it has been discovered that undesirable plants can be controlled by contacting such plants or organisms and/or their habitats with compositions containing an effective growth-controlling amount of at least one of the oxirane compounds disclosed herein. When the germinant seeds and emerging seedlings of many terrestrial plant species are contacted with compositions containing one of the oxirane compounds in dosages sufficient to supply from about 1.0 to about 50.0 pounds (lb) of the compound per acre, a persistent inhibition of the growth of such seeds and seedlings can be obtained.

In selective applications to plants and/or their habitats for the pre-emergent control of the germinant seeds and seedlings of many undesirable plants, especially those of small-seeded grasses in areas planted with the seeds of desired broadleaf plants or supporting the growth of such plants, compositions containing certain of the oxirane compounds in dosages of from about 0.06 to about 10.0 pounds or more of the oxirane compound per acre have been found satisfactory. The application of larger dosages to terrestrial plants and/or their habitats controls the growth of germinant seeds, of all types, including broadleaf plants, as well as grasses. In all selective applications, the exact dosage to be employed is dependent upon the resistance of the broadleaf crop plants or their seeds to the particular oxirane composition employed and related factors.

It has also been found that compositions employing certain of the oxirane compounds at dosages of from about 250 to about 10,000 or more parts by weight per million parts of ultimate treating composition are effective in controlling the growth of the established plants of many plant species. In many instances, the application of the compositions containing certain oxirane compounds in dosages of from about 250 to about 1000 parts per million by weight per million parts of treating composition results in the selective postemergent control of many undesirable plant species, especially those of smallseeded grasses in areas supporting the growth of the established plants of desired crops, e.g., cotton, corn, cultured rice and white winter wheat. In all selective operations, the exact dosage to be employed is dependent upon the resistance of the crop plants to the particular oxirane composition employed and other related factors more fully explained hereinafter.

The application to plants, plant-parts, rooting zones and/or their habitats of a composition containing a growth-suppressing amount of an oxirane compound is essential and critical for the practice of the present invention. The exact dosage to be supplied by the composition in a given operation is dependent upon the plant species and upon the stage of growth and hardiness thereof as well as upon the plant part to be exposed to the pesticidal composition. Other factors, such as for example, the weathering action of rain, can remove the oxirane compound away from the locus of the plant by washing it off the plant leaves or leaching it away from the rooting zone. The compositions and the oxirane compounds contained therein could be decomposed by the action of bacterial and other soil organisms which eventually frees the plant, plant part, and/or their habitats of the active ingredient, must also be considered. Thus, while the application of low amounts of active compounds per acre may be sufficient for good control of a light infestation of weeds growing under adverse conditions, applications of from 5 to 10 pounds or more of active compound per acre may be required for good control of a dense infestation of hardy weeds growing under favorable growth conditions.

Compositions comprising an oxirane compound with an inert material known as an agricultural adjuvant or carrier in solid or liquid form allow the growth-suppressing amount of the active ingredient to be mixed in such quantity of ultimate treating material that adequate coverage of all plants and plant-parts or adequate admixture with their habitats (e.g., soil) can be obtained. An adjuvant is defined herein as any substance in a herbicide formulation or added to the spray tank to improve herbicidal activity or application characteristics. Good growth-suppressing results are obtained when employing a carrier material in relatively small, but effective amounts. Generally, however, the best results are obtained by employing either a surface-active dispersing agent, in an amount sufficient to emulsify the oxirane compound with an organic solvent or with water as a carrier, for example, an amount which represents from 0.1 to 15 percent, by weight, of the total treating material; or a finely divided carrier solid, in an amount which represents from about 40 to about 99.5 percent, by weight, of the total treating material.

The exact concentration of the oxirane compounds employed in the compositions for application to plants, plant-parts and/or their habitats is not critical and can vary considerably provided the required dosage of effective agent is supplied to the plant, plant-part, rooting zone, and/or habitat treated. The concentration of the oxirane compound in liquid compositions employed to supply the desired dosage generally is from about 0.0001 to about 50 percent by weight, although concentrations as high as 90 percent by weight are sometimes conveniently employed. In finely divided solid carrier compositions, the concentration of the oxirane compound can be from 0.1 to 60 percent by weight. In compositions to be employed as concentrates, the oxirane compound can be present in a concentration of from about 5 to about 98 percent by weight.

In preemergent operations for selective uses a dosage of about 0.01 to about 10 lb/acre or more is generally applicable, a rate of 0.05 to 4 lb/acre being preferred and about 1 to about 2 lb/acre being most preferred.

In postemergent operations a dosage of about 0.01 to about 20 pounds/acre or more is generally applicable, although not all compounds are equally effective and some weeds are more difficult to control. A dosage rate in the range of about 0.5 to about 8 lb/acre is preferred, more preferably about 1 lb/acre.

The quantity of treating compositions to be applied can vary considerably provided that the required dosage of active ingredient is applied in sufficient of the finished composition to facilitate the distribution of the active agent on the plant or plant-part, or the penetration of the active ingredient into the plant habitat. The required amount of the active agent conveniently can be supplied per acre treated in from about 10 to 27,000 gallons or more of the liquid carrier or in from about 10 to 2,000 pounds of the finely divided solid carrier.

Liquid compositions employed as a spray containing the desired amount of active ingredient can be prepared by dissolving the oxirane compound in an organic liquid carrier or by dispersing the oxirane compound in water with or without the aid of a suitable surface-active dispersing agent such as an ionic or non-ionic emulsifying agent. Suitable organic liquid carriers include the agricultural spray oils and the petroleum distillates such as diesel fuel, kerosene, fuel oil naphthas and Stoddard solvent. Among the organic liquid carriers, the petroleum distillates are generally preferred. The aqueous compositions can contain one or more water immiscible solvents for the oxirane compound. In such compositions, the carrier comprises an aqueous emulsion, i.e., a mixture of water, emulsifying agent and water immiscible solvent. The choice of dispersing and emulsifying agent and the amount thereof employed is dictated by the nature of the composition and by the ability of the agent to facilitate the dispersion of the oxirane compound in the carrier to produce the desired composition. Dispersing and emulsifying agents which can be employed in the compositions include the condensation products of alkylene oxides with phenols and organic acids, alkyl aryl sulfonates, polyoxyalkylene derivatives of sorbitan esters, complex ether alcohols, mahogany soaps, and the like.

In the preparation of dust compositions, the active ingredient is dispersed in and on a finely divided solid carrier such as clay, talc, chalk, gypsum, bentonite, fuller's earth, attapulgite, and the like. In such operation, the finely divided carrier is mechanically mixed or ground with the oxirane compound. Depending upon the proportion of ingredients, these dust compositions can be employed as concentrates and subsequently diluted with additional solid carrier or with liquid or solid surface-active dispersing agent to obtain the desired amount of active ingredient in a composition adapted to be employed for the suppression of the growth of the plants. Also, such dust compositions, particularly when finely ground or milled, can be dispersed in water, preferably with the aid of a surface-active dispersing agent, to form spray mixtures.

Suitable adjuvants useful in making up compositions of the foregoing type are well known to those skilled in the art. The methods of applying the solid or liquid herbicidal formulations similarly are well known to the skilled artisan.

Satisfactory results are obtained when the oxirane compositions are combined with other agricultural materials intended to be applied to plants, plant-parts and/or their habitats. Such materials include fertilizers, fungicides, insecticides, acaricides, nematocides nematocides, bactericides, soil conditioning agents, other herbicides, usually with a complementary spectrum of weed control, and the like.

When operating in accordance with the present invention, compositions containing growth-suppressing amounts of the oxirane compounds are applied to plants, plant-parts and/or their habitats in any convenient fashion. Applications to a plant habitat, e.g., soil, can be carried out by simply mixing with the habitat, such as by applying to the surface of soil by spraying a liquid composition and thereafter dragging or discing into the soil to the desired depth or by employing a liquid carrier to accomplish the penetration and impregnation. The application of spray and dust compositions to the surface of soil can be carried out by conventional methods, e.g., power dusters, boom and hand sprayers and spray dusters.

In a further method, the distribution of the oxirane compositions in soil can be accomplished by introducing the active ingredient in the water employed to irrigate the soil. In such procedures, the amount of water can be varied with the porosity and water holding capacity of the soil to obtain a desired depth of distribution of the agent.

In addition, the present method also comprehends the employment of an aerosol composition containing an oxirane compound as an active compound. Such a composition is prepared according to conventional methods wherein the active ingredient is dispersed in a solvent, and the resultant dispersion mixed with a readily volatilized liquid propellant. Such variables as the particular active ingredient to be used and the particular plant part to be treated will determine the identity of the solvent and the concentration of the active ingredient therein. Examples of suitable solvents are water, acetone, isopropanol, and 2-ethoxyethanol. Also, employment of the oxirane compound in pastes, gels, foams, invert emulsions, and the like, as well as pigmented or unpigmented pelleted solids is comprehended. The following examples further illustrate the present invention.

EXAMPLES 5-8

Preemergence Operation

Separate aqueous compositions containing 2-(3-chlorophenyl)-2-(2,2-dichloro-3,3-3-trifluoropropyl)oxirane; 2-(3,5-dichlorophenyl)-2-(2,3-dichloro-2,3,3-trifluoropropyl) oxirane; 2-(2,2-dichloro-3,3,3-trifluoropropyl)-2-(3 (trifluoromethyl)phenyl)oxirane; and 2-(3,5-dichlorophenyl)-2-(2,2-dichloro-3,3,3-trifluoropropenyl)oxirane were prepared as follows:

Each compound was dissolved in acetone to one half of the final volume (twice the final concentration) used and the acetone solution in each case was admixed with an equal volume of water containing 0.1 percent by weight of Tween-20 surface active material (Tween-20 is a trademark of Atlas Chemical Company). The composition, generally in the nature of an emulsion, was employed to treat separate respective seed beds of sandy loam soil of good nutrient content wherein each seed bed contained separate groups of good viable seeds, each group being of one of a known plant species. The various beds were positioned side by side and exposed to substantially identical conditions of temperature and light. Each bed was maintained so as to prevent any interaction with the test compound in different seeds beds. Each seed bed was treated with the composition as a spray employing conventional spraying equipment to deposit a predetermined amount of the compound uniformly throughout the surface of the bed. Another seed bed was treated only with the acetone-Tween-20 water mixture with no chemical added to serve as checks. After treatment, the seed beds were maintained for two weeks under greenhouse conditions conducive for good plant growth and watered as necessary. Control refers to the reduction in growth of the test species in the presence of the test chemical relative to the observed growth of the same species in the absence of the test chemical. Two weeks after treatment, the beds were examined for plant growth and evaluated on a scale of 0 to 100. A percent control of "0" indicates there were no visible effects, whereas "100" indicates all plants were dead. A "-" indicates this treatment was not tested. The specific plant species, dosage rate and the percent preemergent control obtained are set forth in Table 1.

TABLE 1

Preemergent Control Of Seed Germination At Various Indicated Herbicidal Concentrations

| Example | Compound | Dosage Rate lb/acre | A | B | C | D | E | F | G | H | I | J | K | L | M | N | O | P | Q | R |
|---|---|---|---|---|---|---|---|---|---|---|---|---|---|---|---|---|---|---|---|---|
| | | | | | | | | | | | % Control | | | | | | | | | |
| 5 | 2-(3,5-dichlorophenyl)-2-(2,2-dichloro-3,3,3-trifluoropropyl)-oxirane | 0.60 | 10 | 30 | — | — | 0 | 100 | — | 20 | 80 | 99 | 0 | 75 | 98 | — | 20 | — | 10 | 0 |
| | | 1.20 | 50 | 60 | 0 | 0 | 20 | 100 | 0 | 35 | 100 | 100 | 10 | 80 | 100 | 0 | 90 | 0 | 25 | 15 |
| | | 10.00 | — | 100 | — | 100 | — | 100 | — | — | 100 | 100 | — | 100 | 100 | — | — | 0 | — | 50 |
| 6 | 2-(3,5-dichlorophenyl)-2-(2,3-dichloro-2,3,3-trifluoropropyl)-oxirane | 0.50 | — | — | — | — | 20 | — | 30 | — | — | 97 | 0 | 50 | 80 | — | — | — | — | — |
| | | 1.00 | 0 | — | 0 | 0 | 80 | — | 40 | — | 20 | 100 | 50 | 90 | 95 | 0 | 0 | 0 | 0 | 0 |
| 7 | 2-(3-chlorophenyl)-2-(2,2-dichloro-3,3,3-trifluoropropyl)-oxirane | 0.50 | 90 | — | 30 | — | 100 | — | 30 | — | 95 | 100 | — | 99 | 90 | — | 100 | — | — | 100 |
| | | 1.00 | 90 | — | 70 | 0 | 99 | — | 85 | — | 100 | 100 | 0 | 100 | 100 | 0 | 99 | 0 | 0 | 100 |
| | | 10.00 | — | 100 | — | 0 | — | 100 | — | — | — | 100 | — | 100 | 100 | — | — | 100 | — | 100 |
| 8 | 2-(2,2-dichloro-3,3,3-trifluoropropyl)-2-(3-(trifluoromethyl)phenyl)oxirane | 0.50 | — | — | — | — | 40 | — | — | — | 20 | 45 | — | 40 | 0 | — | — | — | — | — |
| | | 1.00 | 0 | — | 0 | — | 60 | — | — | — | 95 | 90 | — | 97 | 20 | — | 0 | — | — | — |
| | | 2.00 | 100 | — | — | 0 | 100 | — | 0 | — | 100 | 100 | 0 | 100 | 40 | 0 | 90 | 0 | 0 | 0 |

A = Nutsedge
B = Pigweed
C = Soybean
D = Cotton
E = White Winter Wheat
F = Crabgrass
G = Corn
H = Grain Sorghum
J = Barnyard grass
K = Sugarbeets
L = Wildoats
M = Yellow Foxtail
N = Rape
O = Cultivated Rice
P = Velvet leaf
Q = Jimson Weed TABLE 1-continued

| | | Dosage Rate lb/acre | Preemergent Control Of Seed Germination At Various Indicated Herbicidal Concentrations | | | | | | | | | | | | | | | | |
|---|---|---|---|---|---|---|---|---|---|---|---|---|---|---|---|---|---|---|---|
| | | | Plant Species | | | | | | | | | | | | | | | | |
| Example | Compound | | A | B | C | D | E | F | G | H | I | J | K | L | M | N | O | P | Q | R |
| | | | | | | | | | | % Control | | | | | | | | | | |

I = Johnsongrass      R = Morninglory

EXAMPLES 9–11

Postemergence Operations:

Representative compositions of the present invention were evaluated for the postemergence control of various plant species. In these evaluations, plots of the plant species used in Examples 5–8 were grown to a height of about 4 inches. Aqueous spray compositions, containing oxirane compounds in concentrations of 500 ppm, 4000 ppm and 10,000 ppm, respectively, were applied to separate plots. These concentrations correspond to approximately 1, 8, and 20 pounds active ingredient per acre. The spray compositions were made by mixing the active ingredient in acetone to ½ the final volume, i.e. twice the final concentration. An equal amount of water was added to the active ingredient/acetone mixture wherein the water contained 0.1 percent by weight of TWEEN ® 20 surfactant. The application to the plants was made to the point of run-off and was carried out with conventional spraying equipment. Other plots were sprayed with similar compositions containing no toxicant to serve as checks. Thereafter, the plots were maintained under conditions conducive for plant growth. Two weeks after treatment, the plots were examined for plant growth and evaluated on a scale of 0 to 100 where "0" represents no visible effect and "100" represents complete kill. The results of the examination of the treated plots are set forth below in Table 2.

What is claimed is:

1. A substituted styrene compound of the formula

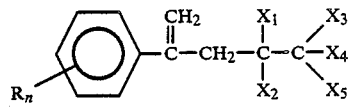

wherein n is an integer from 0 to 5; R independently represents halogen or -CF$_3$; and X$_1$, X$_2$, X$_3$, X$_4$, and X$_5$ each independently represent halogen.

2. The compound according to claim 1 wherein n is 1 to 2.

3. The compound according to claim 2 wherein R is chlorine.

4. The compound according to claim 2 wherein R is —CF$_3$.

5. The compound according to claim 1 which is 1,3-dichloro-5-(3,3-dichloro-4,4,4-trifluoro-1-methylene butyl)benzene.

6. The compound according to claim 1 which is 1-chloro-3-(3,3-dichloro-4,4,4-trifluoro-1-methylene butyl)benzene.

7. The compound according to claim 1 which is 1-trifluoromethyl-3-(3,3-dichloro-4,4,4-trifluoro-1-methylene butyl)benzene.

8. The compound according to claim 1 which is 1,3-dichloro-5-(3,4-dichloro-3,4,4-trifluoro-1-methylene butyl)benzene.

* * * * *

TABLE 2

| Example | Compound | Dosage Rate -ppm- | Preemergent Control Of Seed Germination At Various Indicated Herbicidal Concentrations | | | | | | | | | | | | | | | | |
|---|---|---|---|---|---|---|---|---|---|---|---|---|---|---|---|---|---|---|---|
| | | | Plant Species | | | | | | | | | | | | | | | | |
| | | | A | B | C | D | E | F | G | H | I | J | K | L | M | N | O | P | Q | R |
| | | | | | | | | | | | % Control | | | | | | | | | |
| 9 | 2-(3,5-dichlorophenyl)-2-(2,2-dichloro-3,3,3-trifluoropropyl)oxirane | 500 | 0 | 0 | 0 | 30 | 0 | 90 | 0 | 0 | 0 | 0 | 0 | 0 | 80 | 0 | 0 | 0 | 0 | 0 |
| | | 4000 | 0 | 0 | — | 0 | — | 90 | — | — | — | 80 | — | 70 | 90 | — | — | 0 | — | 0 |
| 10 | 2-(3,5-dichlorophenyl)-2-(2,3-dichloro-2,3,3-trifluoropropyl)oxirane | 500 | 0 | 0 | 60 | 0 | 0 | 0 | 0 | 0 | 90 | 0 | 0 | 0 | 70 | 50 | 40 | 0 | 0 | 0 |
| 11 | 2-(3-chlorophenyl)-2-(2,2-dichloro-3,3,3-trifluoropropyl)oxirane | 500 | 0 | 0 | 0 | 0 | 0 | 80 | 0 | 0 | 100 | 0 | 0 | 0 | — | 0 | 0 | 0 | 0 | 0 |
| | | 10,000 | 45 | 100 | — | 0 | — | 90 | — | — | — | 80 | — | 80 | 80 | — | — | 0 | — | 0 |

A = Nutsedge
B = Pigweed
C = Soybean
D = Cotton
E = White winter wheat
F = Crabgrass
G = Corn
H = Grain Sorghum
I = Johnsongrass
J = Barnyard grass
K = Sugarbeets
L = Wild Oats
M = Yellow Foxtail
N = Rape
O = Cultivated Rice
P = Velvet leaf
Q = Jimson weed
R = Morninglory